United States Patent [19]
Yuen et al.

[11] Patent Number: 6,038,478
[45] Date of Patent: Mar. 14, 2000

[54] LYMPHOCYTE ATTRACTION BY ELECTRICAL STIMULATION

[75] Inventors: Ted G. H. Yuen, Los Angeles; William F. Agnew, Altadena; Douglas B. McCreery, Pasadena; Leo A. Bullara, Glendora; Marylou Ingram, Pasadena, all of Calif.

[73] Assignee: Huntingdon Medical Research Institutes, Pasadena, Calif.

[21] Appl. No.: 09/173,901

[22] Filed: Oct. 16, 1998

Related U.S. Application Data

[60] Provisional application No. 60/062,177, Oct. 16, 1997.

[51] Int. Cl.[7] ........................................................ A61N 1/32
[52] U.S. Cl. ............................................ 607/74; 128/898
[58] Field of Search .................................. 607/115, 116, 607/139, 2, 45, 46, 48, 50, 58, 70, 72, 74

[56] References Cited

U.S. PATENT DOCUMENTS

| | | | |
|---|---|---|---|
| 5,215,088 | 6/1993 | Normann et al. | 600/377 |
| 5,814,078 | 9/1998 | Zhou et al. | 607/1 |
| 5,817,138 | 10/1998 | Suzuki et al. | 607/67 |

*Primary Examiner*—Jeffrey R. Jastrzab
*Attorney, Agent, or Firm*—Christie, Parker & Hale, LLP

[57] ABSTRACT

The invention is a method of attracting lymphocytes to at least one desired location in the body of a patient for a therapeutic purpose (e.g., treating infection or inflammation, killing tumor cells, etc.), the method comprising contacting the desired location with one or more electrodes and stimulating the tissue with current at an intesity below that which will physically damage the cells, yet sufficient to attract lymphocytes.

9 Claims, 6 Drawing Sheets

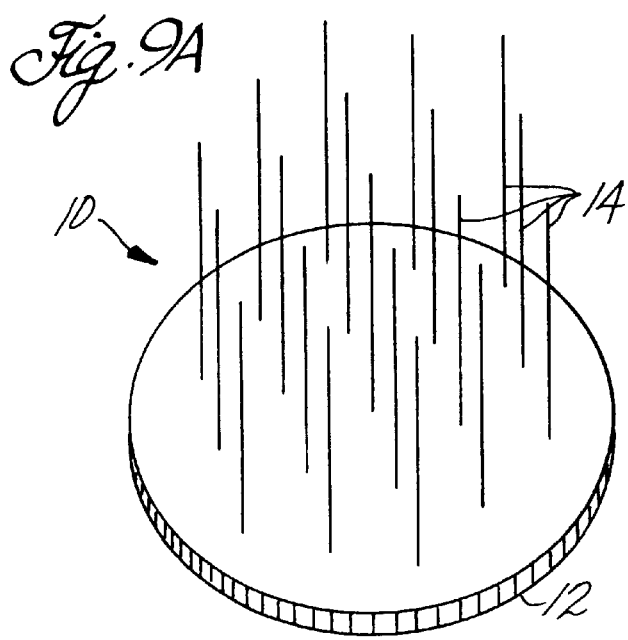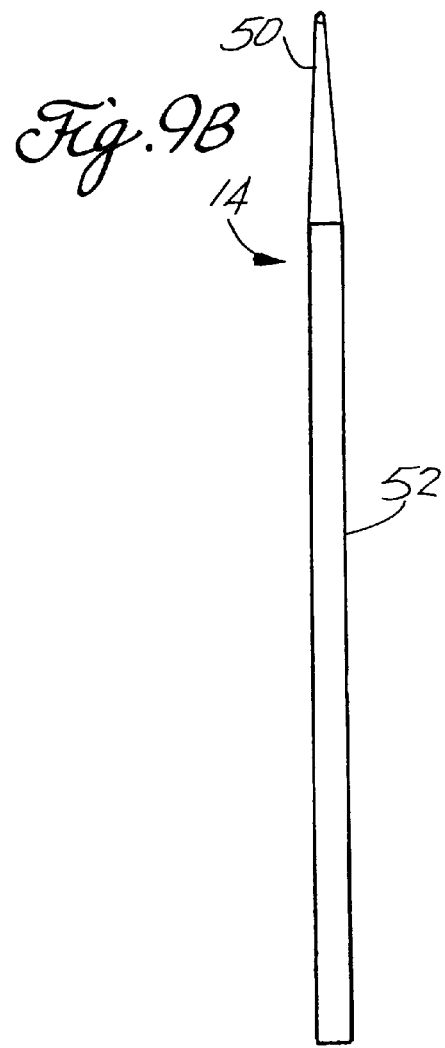

LYMPHOCYTE ATTRACTION BY ELECTRICAL STIMULATION

This application claims the benefit of Provisional Application No. 60/062177 filed Oct. 16, 1997.

This invention was made with government support under Contract #N 01NS-82388 awarded by the National Institutes of Health. The government has certain rights in the invention.

BACKGROUND OF THE INVENTION

The field of the invention is enhancement of natural immune response, specifically the localization of aggregates of lymphocytes in desired regions of the body by application of electrical stimulation.

Stimulation of the body's own immune defenses to ward off infection or to attack tumors is preferable in many cases to chemical or surgical intervention, or can be useful to augment such therapies. For example, chemotherapeutic agents often act to inhibit cell division, in order to slow tumor growth sufficiently to allow the normal immune response to eliminate tumor cells. Such chemotherapeutic agents are not specific for tumor cells and also inhibit normal cell division, leading to prodigious toxic side effects. In other cases, tumors, particularly of the brain, are inaccessible surgically or can be only partially resected. Moreover, tumors in the brain tend to be sealed off from the immune system by the blood-brain barrier which sharply curtails access of circulating immune cells to the brain. A method of stimulating an immune response against cells which have undergone neoplastic transformation, for example, would augment the effectiveness of various chemical and surgical interventions, reducing side effects and improving outcome.

Effector lymphocytes responsible for cellular immune responses can be classified into three major classes, namely NK (natural killer) cells, a minority population, and helper/inducer (T4) and suppressor/cytotoxic (T8) cells, which together make up the majority of lymphocytes in the circulating blood. T lymphocytes and natural killer cells effect cell mediated immunity. B lymphocytes differentiate into plasma cells that produce antibodies specific for the stimulating antigen. Antibody production is referred to as humoral immunity. Upon activation, T cells proliferate and are released into the circulation and thence ultimately reach tissues. Generally, lymphocytes are activated only in response to a specific antigen, but artificial means of activating them have been found, for example, lectins such as Concanavalin A and electrical stimulation (Bourguignon et al., *J. Cellular Biochem.* 37:131–150, 1988).

Natural killer cells can directly attack tumor cells and cells that have been invaded by viruses. Cytotoxic T cells also attack tumor cells and virus-infected cells by binding to the antigen-bearing target cell. To bind and activate the T cell however, the foreign antigen must first be processed and presented to the cytotoxic T cell in the context of the appropriate histocompatibility complex molecule (MHC). Other adhesion molecules on the membranes of the T cells and their target cells also assist in the binding and activation of the T cells. Ultimately the activated T cell, like the NK cell, kills the target cell by constructing pores in the target cell membrane and inducing death by apoptosis. Helper T cells act to increase the activation of macrophages, B cells and other T cells by secreting lymphokines (interleukin-2, gamma-interferon, etc.). This enhances the efficacy of the lymphocyte response in tumored or infected tissue. Suppressor T cells modulate the response of other T cells to prevent excessive or auto-immune reactions.

The use of electrical stimulation to promote bone and soft tissue healing is known (see e.g., J. Black, *Clin. Plast. Surg* Apr. 12, 1885 (2):243–57).

The therapeutic value of stimulated lymphocytes to treat brain tumors is known; for example U.S. Pat. No. 4,902,288 (incorporated by reference) describes immunotherapy for tumors using implantable, stimulated lymphocytes. Use of the instant invention to enhance the number and improve the distribution of lymphocytes to all areas of a tumor, including the invading edge, such as in the brain following surgical debulking of a tumor or in an inoperable tumor, could substantially improve or replace traditional therapies, and lead to enhanced patient survival and quality of life.

SUMMARY OF THE INVENTION

The invention is an electrode array and a method of using it to attract lymphocytes to a selected location in the body of a patient, the method comprising applying the electrode array to the desired locations in the body, and applying current through one or more of the electrodes in the array at an intensity below that which will physically damage cells.

The electrode array of the invention contains multiple electrodes, one, some, or all of which may be used for tissue stimulation, and some of which may be used for stabilizing the array in the tissue. Each electrode in the array used to pass current in a given protocol can be wired in parallel to deliver the applied current protocol simultaneously from one source, or each active electrode can be independently connected to a stimulating device, allowing each electrode to deliver the same or a different protocol on any time interval or with any phase shift desired.

Preferably, in the method of the invention, the electrical stimulation is provided in charge balanced pulses, and preferably the stimulation frequency is less than 1000 Hz and the pulses are between 25 $\mu$sec–1000 msec each. Preferably, the charge density of the pulses is between 0–5000 $\mu$Coulomb/cm$^2$.

In a preferred embodiment, the electrode is a part of an array comprising a plurality of electrodes; alternatively, the electrode is a plate or mesh array.

In a particularly preferred embodiment, the invention is a method of reducing the number of tumor cells in a patient comprising attracting lymphocytes to one or more selected locations in the patient's body by applying the electrode array to the selected location, and applying current through one or more electrodes at an intensity below that which will physically damage cells.

DESCRIPTION OF THE DRAWINGS

FIG. 9A shows a preferred electrode array of the invention.

FIG. 9B shows a side view of an individual electrode which may be used in the electrode array of the invention.

DETAILED DESCRIPTION OF THE INVENTION

Figure 1:
FIG. 1 is a topical view of a preferred electrode array implanted in brain tissue.

The present invention provides for a non-toxic, minimally invasive method and apparatus to stimulate the naturally occurring immune response to pathologic conditions such as cancer or certain types of localized infections. It can be used alone or in combination with traditional therapies such as chemotherapy, antibiotics, and surgery, and may provide the advantage of minimizing use of such traditional therapies.

In the method of the invention, lymphocytes are attracted to a desired site in the body of a patient suffering from e.g., an infection or a solid tumor by application of current through one or more electrodes placed at the site. The lymphocytes may be previously activated by exposure to circulating antigens, or may be activated at the site by the applied electrical stimulus or antigenic or activating substances in the locale (endogenous or applied).

The electrodes for use in the invention may be any which are suitable for implantation into the body of an animal, for example, the electrodes and their methods of fabrication described in U.S. Pat. Nos. 3,826,244, 5,215,088, and 5,524, 338, all herein incorporated by reference. Appropriate metals and compositions for use in the electrodes include iridium, platinum, titanium, rhodium, gold, carbon, and oxides of these elements (e.g., iridium/iridium oxide, a preferred composition). Ideal characteristics of the electrode or electrode array (e.g., size, shape, number of contact sites) may vary depending on the type of tissue where it is to be implanted. The Examples included in this specification describe an array of seven separate electrodes in an array, and are suitable for use in the brain, perhaps the most delicate tissue in which to practice the invention. However, essentially any number of electrodes may be used in an array, and many other electrode configurations are suitable, such as plate electrodes, deformable insulated mesh, with the insulation removed at desired contact points, or single electrodes such as described in U.S. Pat. No. 3,826,244, supra. For elongated (cylindrical) electrodes, preferred individual electrode diameters are between 20–1000 µm; preferred electrode length is between 0.1–1000 mm, although parameters vary with tissue type and desired depth of penetration. The electrode array has at least one stimulating electrode (through which current is passed) and one stabilizing electrode (through which current may optionally be passed, but which serves also to hold the array in position within the tissue). Plate or mesh electrodes can be of a size suitable to treat the involved area, or if insulated, can have uninsulated contact regions of any desired area. For example, an insulated flexible mesh electrode might have the insulation removed on the side of the mesh adjacent to a solid tumor, and over an area in contact with any number of tumor cells.

The invention can be used to attract lymphocytes to sites anywhere in the body which are accessible by any surgical techniques (including remote placement using devices such as catheters or endoscopes), and is also suitable for topical or subcutaneous application. As such, it is useful in the treatment of solid tumors, either alone or in combination with previous surgical, chemical, and/or radiotherapies; or in the treatment of certain infections, especially in poorly vascularized or inaccessible areas; or any condition where surgical intervention is unadvised or impossible (e.g., prostate cancer or certain brain tumors) and electrode placement is feasible and less destructive. The method of this invention may also be used in conjunction with any means known in the art to stimulate lymphocyte activation.

Stimulation protocols can be as long as necessary, but efficacious protocols may be less than 10 minutes. Generally, preferred protocols will be under 8 hours in duration, and may be repeated, as electrode placement can be chronic. Preferred current densities are in the range of 200–2000 $\mu$Coulombs/cm$^2$, more preferably 800–1600 $\mu$C/cm$^2$ (2–8 nC/phase), although this range can be extended greatly (to just below the point of tissue damage) depending on the type of tissue and its susceptibility to injury by electrical stimulation. In a preferred embodiment, current is applied in charge-balanced pulses of between 150–400 $\mu$sec/pulse. Stimulation protocols and current spread can be optionally monitored by a recording electrode at a nearby site.

The following examples are intended to be illustrative of the method and are not intended to be limiting.

EXAMPLE 1
Preferred Microelectrodes for Intracortical Stimulation

Referring to FIGS. 9A and 9B, the electrodes are assembled into arrays 10. Preferably, a Teflon mold is fabricated that holds the tip end 50 and the shaft 52 of each of up to 19 electrodes in one preferred embodiment. The electrodes are preferably between 1–100 µm in diameter, more preferably between 32–36 µm in diameter. The tip is preferably angled at about 10 degrees, and the terminus of the tip is preferably between 0.1–50 µm radius, more preferably between 3–8 µm radius. Preferably, about 500 µm$^2$ is exposed at the tip. The mold holds the electrodes in separate alignment tubes, spaced 380 µm apart (center to center). The alignment tubes are laid out in a 1-6-12 concentric pattern and installed flush with the bottom of a 0.5 mm deep×2.5 mm diameter cavity. The individual electrode shafts are inserted tip first into the teflon tubes, to a depth defined by the weld junctions at the upper end of the shaft. Shafts can be any length, but are preferably between 1–4 mm long. The upper portion of the array of shafts is encapsulated in medical grade 2-part Epoxy (Masterbond EP21ILY) to form the support matrix for the array of electrodes. The teflon tubing can be crimped to securely hold the electrodes in the array.

In another preferred embodiment, shown in FIG. 1, intracortical arrays contain seven discrete activated iridium microelectrodes extending from a button of Hysol epoxy, approximately 2.5 mm in diameter. The microelectrode shafts are spaced 380 µm apart center to center. The shaft in the center of the cluster is 2 mm in length. Three of the shafts are 1.5 mm in length, and three are 1.7 mm in length. The uninsulated iridium shafts are 32–50 µm in diameter, preferably 32–37 µm. The shafts are coated with Epoxylite insulation prior to implantation, leaving the tips exposed for electrical contact with the tissue. Alternatively, if the entire electrode is coated during the insulating process, the tips (or any desired region) can be exposed by abrasion, chemical or laser etching, or other means. The conical tips of the microelectrodes have radii of curvature of 5–6 µm. The geometric area of the exposed tips is 450 µm$^2$, ±10%. The arrays are integrated with a 16-pin percutaneous connector 18 (see FIG. 1) that also includes a large indifferent platinum electrode. The complete assembly is soaked in deionized water for 48 hours, then sterilized with ethylene oxide.

EXAMPLE 2

Example of Surgical Implantation of Electrodes in the Brain

The intracortical arrays described in Example 1 were implanted into seven young adult cats using general anesthesia and aseptic surgical technique. The animals' heads were mounted in a stereotaxic holder, the scalp and muscles were reflected in a midline incision, and the pericruciate gyri (sensorimotor cortex) exposed. The percutaneous connector was mounted to the skull with stainless steel screws and methacrylate bone cement. a microstimulating electrode was placed on the dura over the postcruciate gyrus, and a recording electrode was implanted into the pyramidal tract through a small burr hole over the cerebellum. The large pyramidal tract potential evoked from the surface of the postcruciate gyrus was used to guide the recording electrode into the tract. The recording electrode was then sealed to the skull using methacrylate bone cement.

A small flap, slightly larger than the array's superstructure, was made in the dura over the postcruciate cortex, and the array of microelectrodes was inserted manually into the cortex by grasping its cable with padded forceps while pushing the array into the brain. The dura was not sutured over the array, but the array was covered with a sheet of perforated artificial dura (silastic sheeting). The cortex was then covered with Gelfoam and the skull defect sealed with cranioplasty. Animals were allowed to recover completely.

EXAMPLE 3

Example of Efficacious and Safe Stimulation Protocol in the Brain

At least 45 days after implantation, a test stimulation regimen was conducted, with the animal lightly anesthetized with Propofol. Before and after the test stimulation, the response evoked by the intracortical microelectrodes was recorded from the pyramidal tract. By this method, it was determined that the anesthesia does not reduce the amount of neural activity evoked by the microelectrodes, and that it does not induce an elevation of the electrical threshold of the cortical neurons. The stimulation regimens were seven hours in duration. The electrodes were pulsed continuously with charge-balanced, controlled-current, cathodic-first pulses. The pulse duration was 150–400 $\mu$sec/phase. In most animals, five microelectrodes were pulsed and two were left as unpulsed controls (in one animal, all seven were pulsed). To assess the role of "mass action" on neural damage and/or the lymphocytic accumulation, only one electrode was pulsed in one animal and only two in another. In most animals, the microelectrodes were pulsed simultaneously, but they were pulsed in the interleaved mode in two animals. The stimulus parameters for each animal are listed Table 1 below.

| Animal IC# | Days Post-Implant | # Electrodes Pulsed | Mode | Freq (Hz) | I ($\mu$A) | Charge/phase (nC) | Pulse Duration ($\mu$sec) | Shaft Diameter ($\mu$m) |
|---|---|---|---|---|---|---|---|---|
| 149 | 87 | 7 | simuit | 200 | 20 | 8 | 400 | 50 |
| 150 | 140 | 1 | — | 200 | 20 | 8 | 400 | 50 |
| 153 | 45 | 5 | simult | 200 | 20 | 8 | 400 | 35 |
| 156 | 90 | 5 | simult | 50 | 20 | 9 | 400 | 35 |
| 158 | 77 | 5 | interlv | 200 | 20 | 8 | 400 | 35 |
| 161 | 50 | 5 | interlv | 200 | 53 | 8 | 150 | 35 |
| 162 | 58 | 2 | simult | 200 | 20, 10 | 8, 4 | 400 | 35 |

EXAMPLE 4

Histology

Within 45 minutes after the end of the stimulation, the cats were anesthetized with Nembutal and perfused through the ascending aorta with ½ strength Karnovsky's fixative or buffered paraformaldehyde fixative.

Histologic evaluations were carried out on serial 8 $\mu$m thick paraffin sections cut in the horizontal plane (perpendicular to the electrode shafts). The sections included both pulsed (left) and pulsed (right) cruciate gyri. Serial sections were taken along the entire electrode shaft, although evaluation of the tissue at the pulsed tips was considered most critical. At 100 $\mu$m intervals below the pial surface, we recorded the presence of any inflammatory cells, hemorrhage, cavitation, scarring, gliosis, edema, sheath thickness, as well as the condition of the neurons and the appearance of blood vessels in the area at these levels.

General Observations

Figure 2:
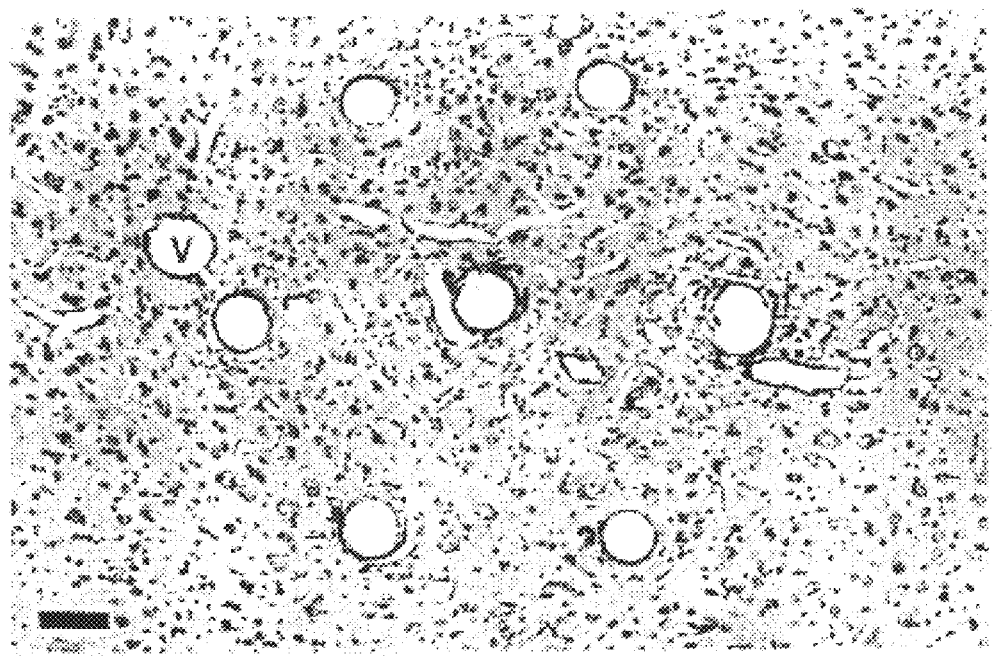
FIG. 2 is a cross section of the postcruciate gyrus following removal of the electrode array, showing the electrode tracks.
Figure 3:
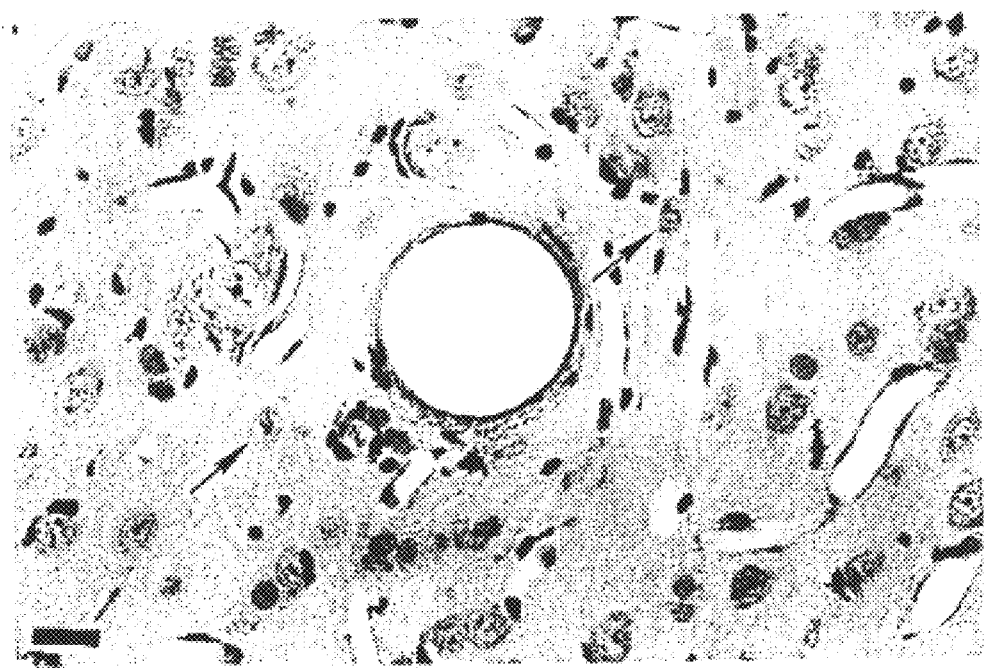
FIG. 3 is a cross-sectional view of one electrode track.
Figure 4:
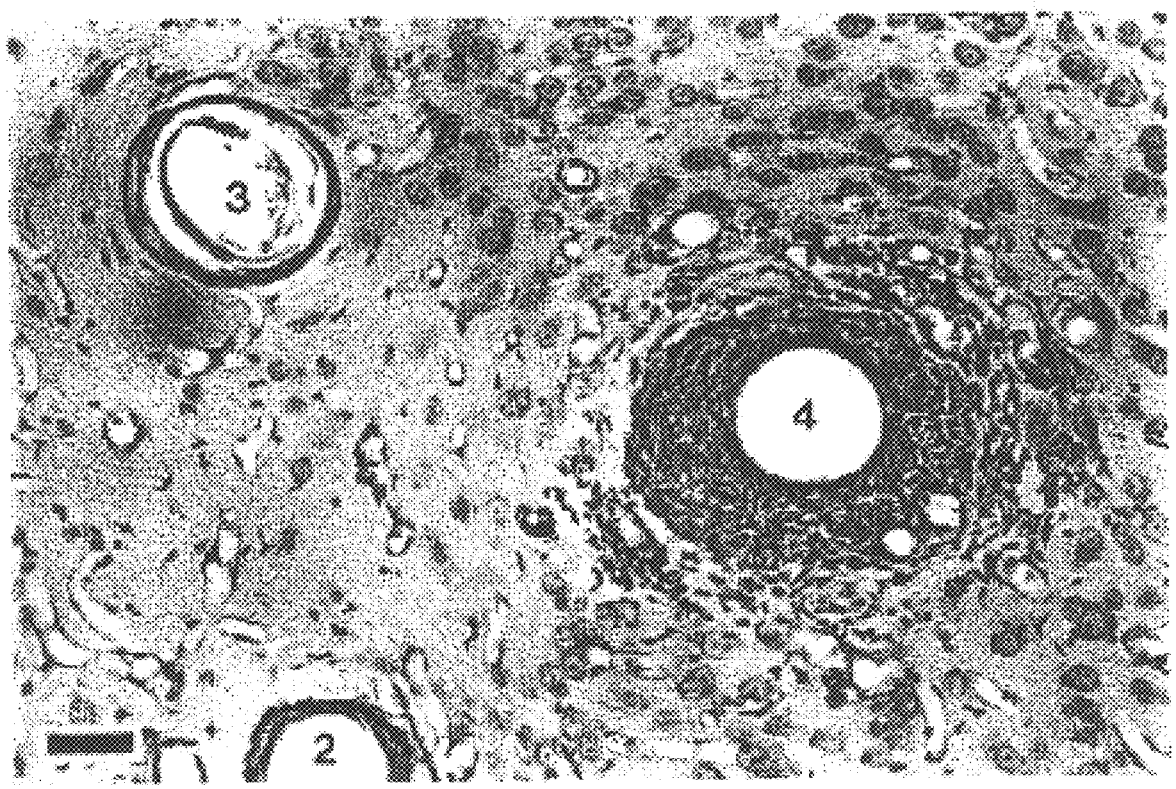
FIG. 4 shows vascular hypertrophy around two tracks ("V").

Following procedures such as those described above, there was usually a shallow cortical impression of the array matrix, although the array was relatively level with the pial surface. The entry sites of the seven electrodes were usually visible with a dissecting microscope and in all cases were free of hemorrhage or infection. All histological evaluations were conducted blind, without knowledge of which electrodes had been pulsed. Representative horizontal sections taken through the electrode tracks of the array shown in FIG. 1 are visible in a hexagonal pattern at a depth of 300 $\mu$m in FIGS. 2 and 3. The connective tissue sheath surrounding the tracks was very thin (generally 3–8 $\mu$m). With few exceptions, there were no hemorrhages, cavitations, or glial scars in any of the animals. When such changes were present, they were small and appeared inconsequential.

In most cases, gliosis was very sparse at the electrode tips with no instance of gliotic scarring at the tips or along the shafts of the microelectrodes. Where gliosis occurred, it was surrounding the shafts of the electrode, and was never adjacent to all the electrodes in any one array. Thus, it did not interfere with current flow. Most animals had a few slightly flattened neurons along the shaft, probably as a result of tissue displacement by the electrode. However, where the tips of electrodes surrounded by a sphere of packed lymphocytes up to 200 $\mu$m in diameter, the exact state of the local neurons was obscured. Evidence of displacement of neurons into the surrounding neuropil was not observed.

Lymphocytic aggregation

Figure 5:
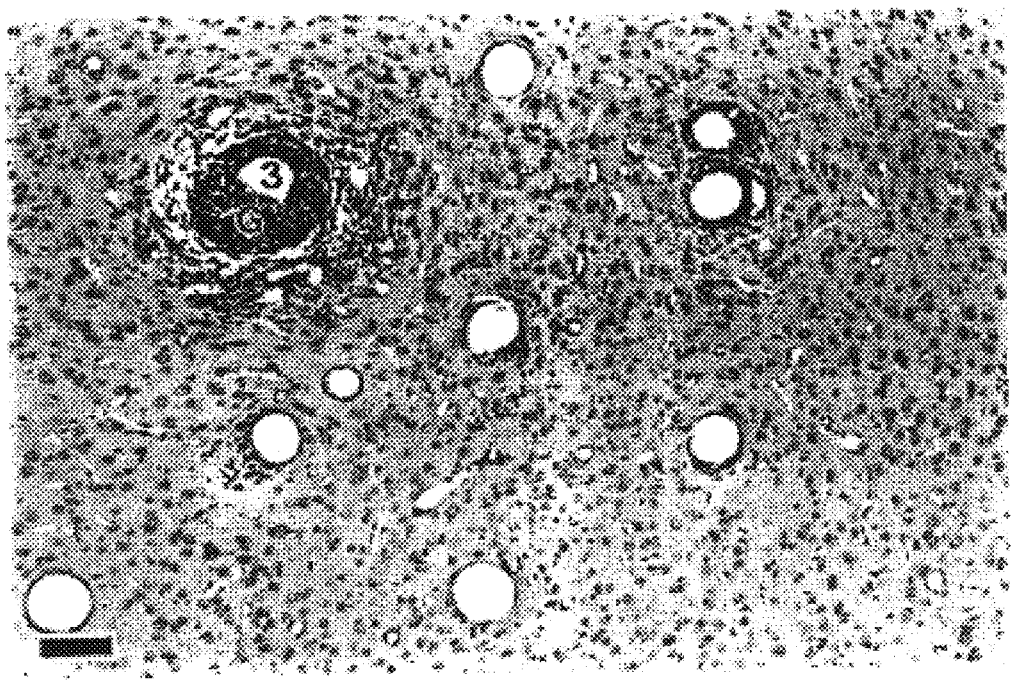
FIG. 5 shows accumulation of lymphocytes at three of five pulsed electrode tip sites.
Figure 6:
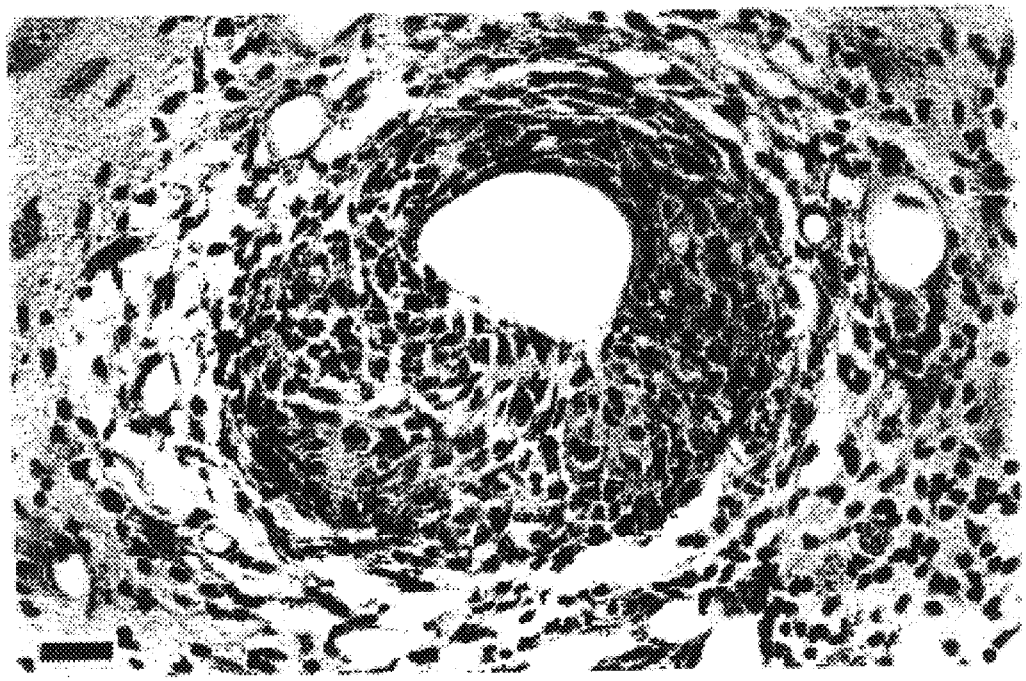
FIG. 6 shows aggregates of lymphocytes around a pulsed tip site.

The predominant histologic feature in the described series of experiments was the occurrence of large numbers of lymphocytes, densely aggregated at the microelectrode tips, and especially at the tips of pulsed electrodes. In all cases in which more than 100 lymphocytes were present in a histologic section, the electrodes had been pulsed at 8 nC. Lymphocytes around unpulsed electrodes never exceeded 50 in a histologic section. The aggregates extended approximately 100–300 $\mu$m above and below the tip (FIGS. 5 and 6). All pulsed electrodes, with two exceptions, were pulsed at 200 Hz, 20 $\mu$A, pulse durations of 400 $\mu$sec (8 nC/phase) and pulsed in a continuous, simultaneous mode. The microelectrodes in two animals (IC-158 and IC-161) were pulsed with the same parameters but in an interleaved mode, and those in IC-161 were pulsed at 50 Hz. Regardless of simultaneous or interleaved pulsing, or at the varying frequencies used here, lymphocyte aggregation occurred at the same magnitude. Lymphocytes aggregated at the tips of the pulsed microelectrodes.

Figure 7:
FIG. 7 shows lymphocyte cuffing of a blood vessel near a pulsed electrode site, and migration of lymphocytes to that site.
Figure 8:
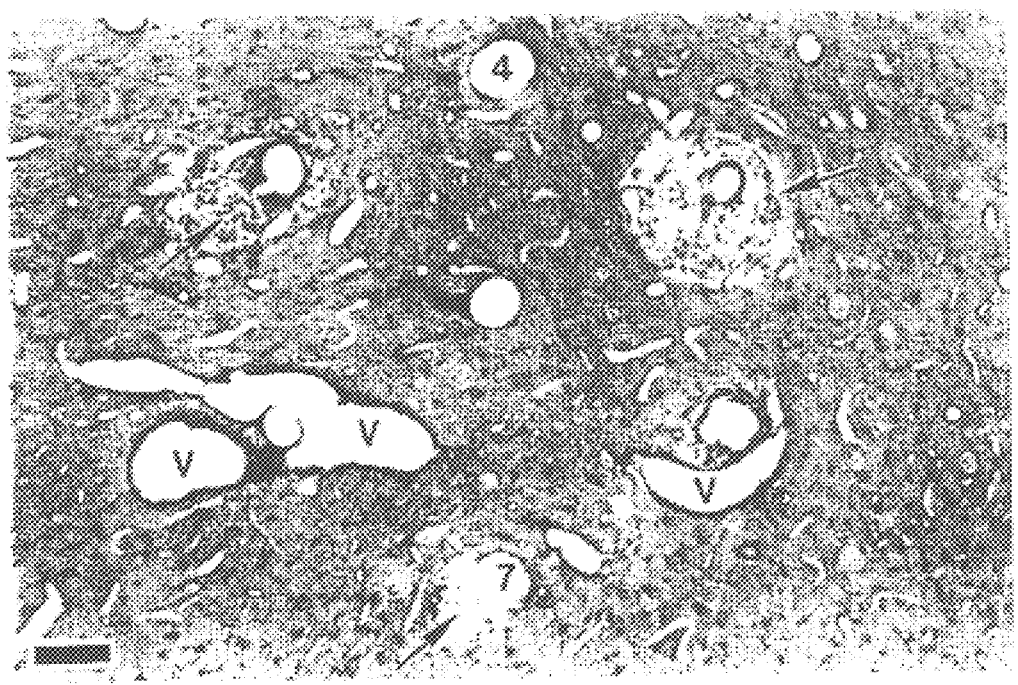
FIG. 8 shows lymphocytes streaming from nearby blood vessel toward a pulsed electrode site, skirting a mass of glial cells.

At the sites of the lymphocytic aggregates, nearby blood vessels showed marked perivascular cuffing and often there was streaming of lymphocytes toward an adjacent pulsed electrode (FIG. 7). In one instance, the emigration of lymphocytes was unable to penetrate a thick cluster of glial cells ensheathing the shaft of the microelectrode a short distance from the tip (FIG. 8).

EXAMPLE 5
Treatment of a Human with Resected Brain Tumor

In the use of the invention in a human patient whose malignant brain tumor has been resected, as much of the tumor as possible is removed surgically, then a plurality of iridium wire electrodes are inserted into the brain tissue around the entire perimeter of the surgical resection. A large platinum indifferent electrode is implanted under the skin, in another part of the body for the duration of the treatment. Each of the wire electrodes is attached to a current source. In a preferred embodiment, each wire is attached to its own current source, so that the current is applied evenly through all of the electrodes.

Trauma and microhemorrhages resulting from electrode insertion is minimized by omitting suturing of the dura and the use of artificial dura and Gelfoam. The configuration of the conical electrode tip (about 12 $\mu$m in diameter) and decreased electrode shaft size (about 35 $\mu$m in diameter) considerably lessens the disruption of small blood vessels in the brain.

In the use of the invention, it does not matter how many electrodes of an array are pulsed, as aggregates in the above Examples 1–4 were just as dense when two electrodes of seven were pulsed as when five of seven were pulsed. Stimulus pulse duration (150–400 $\mu$sec) and frequency (50–200 Hz) also did not matter in these Examples.

Perivascular cuffing by lymphocytes is a prominent feature of the aggregation phenomenon. The method of the invention may result in increased local vascularization, which may in fact enhance the aggregation of lymphocytes.

The preceding description has been presented with reference to presently preferred embodiments of the invention. Workers skilled in the art and technology to which this invention pertains will appreciate that alterations and changes in the described methods and structures may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A method of attracting lymphocytes to a selected location in the body of a patient, the method comprising:

contacting the location with an electrode array comprising at least one stimulating electrode and one stabilizing electrode, the electrodes being rigidly connected by a non-conducting material, each electrode being connected to an external current delivery and recording system, and applying electrical stimulation through the electrode at an intensity below that which will physically damage cells and which is at a level sufficient to attract lymphocytes to the selected location.

2. The method of claim 1 wherein the electrical stimulation is applied in charge balanced pulses.

3. The method of claim 2 wherein the stimulation frequency is less than 1000 Hertz and the pulses are between 25 $\mu$sec–1000 msec each.

4. The method of claim 2 wherein the charge density of the pulses is between 0–5000 $\mu$coulomb/cm$^2$.

5. The method of claim 1 wherein the electrode configuration is selected from the configurations plate, mesh or cylindrical.

6. A method of reducing the number of tumor cells in a patient comprising attracting lymphocytes to a selected location in the patient's body by contacting the location with an electrode array comprising at least one stimulating electrode and one stabilizing electrode, the electrodes being rigidly connected by a non-conducting material, and each electrode being connected to an external current delivery and recording system and applying electrical stimulation through the electrode at an intesity below that which will physically damage cells and which is at a level sufficient to attract lymphocytes to the selected location.

7. The method of claim 6 wherein the electrical stimulation is applied in charge balanced pulses.

8. The method of claim 7 wherein the stimulation frequency is less than 1000 Hertz and the pulses are between 25 $\mu$sec–1000 msec each.

9. The method of claim 7 wherein the charge density of the pulses is between 0–5000 $\mu$C/cm$^2$.

* * * * *

UNITED STATES PATENT AND TRADEMARK OFFICE
CERTIFICATE OF CORRECTION

PATENT NO.   : 6,038,478
DATED        : March 14, 2000
INVENTOR(S)  : Ted G.H. Yuen; William F. Agnew; Douglas B. McCreery; Leo A. Bullara; Marylou Ingram It is certified that error appears in the above-identified patent and that said Letters Patent is hereby corrected as shown below:

Title page,
Item [73], Assignee should read:
-- Huntington Medical Research Institutes, Pasadena, Calif. --

Signed and Sealed this

Fifth Day of February, 2002

Attest:

*Attesting Officer*

JAMES E. ROGAN
*Director of the United States Patent and Trademark Office*